(12) United States Patent
Mohl et al.

(10) Patent No.: US 12,303,387 B2
(45) Date of Patent: May 20, 2025

(54) IMPLANT FOR IMPROVING COAPTATION OF AN ATRIOVENTRICULAR VALVE

(71) Applicant: AVVIE GMBH, Vienna (AT)

(72) Inventors: Werner Mohl, Altenmarkt-Thennenberg (AT); Jeremy Douglas Jarman, Vienna (AT); Preyen Agasthian Perumall, Vienna (AT)

(73) Assignee: AVVIE GMBH, Vienna (AT)

( * ) Notice: Subject to any disclaimer, the term of this patent is extended or adjusted under 35 U.S.C. 154(b) by 0 days.

(21) Appl. No.: 18/716,196

(22) PCT Filed: Nov. 23, 2022

(86) PCT No.: PCT/IB2022/061323
§ 371 (c)(1),
(2) Date: Jun. 4, 2024

(87) PCT Pub. No.: WO2023/105334
PCT Pub. Date: Jun. 15, 2023

(65) Prior Publication Data
US 2024/0415641 A1   Dec. 19, 2024

(30) Foreign Application Priority Data
Dec. 7, 2021   (EP) ..................................... 21020620

(51) Int. Cl.
*A61F 2/24*   (2006.01)
(52) U.S. Cl.
CPC ............ *A61F 2/2418* (2013.01); *A61F 2/246* (2013.01); *A61F 2220/0008* (2013.01)
(58) Field of Classification Search
CPC ...... A61F 2/246; A61F 2/2466; A61F 2/2463; A61F 2/2418; A61F 2/2427;
(Continued)

(56) References Cited

U.S. PATENT DOCUMENTS 9,295,552 B2 *   3/2016   McLean ................ A61F 2/2409
9,592,118 B2 *   3/2017   Khairkhahan .......... A61L 27/50
(Continued)

FOREIGN PATENT DOCUMENTS

EP            3620133 A1 *   3/2020  ............. A61F 2/246
WO   WO-2020148755 A1 *   7/2020  ............ A61F 2/2418

OTHER PUBLICATIONS

International Search Report and Written Opinion received in PCT/IB2022/061323 dated Dec. 21, 2022, p. 10.
(Continued)

*Primary Examiner* — Seema Mathew
(74) *Attorney, Agent, or Firm* — Liang & Hennessey LLP; Brian Hennessey

(57) ABSTRACT

Implant for improving coaptation of an atrioventricular valve in a human heart, the atrioventricular valve having a first and a second native leaflet, an anterolateral and posteromedial commissure between the first and the second native leaflet, and an annulus adjacent a wall of an atrium of the heart. The implant including a frame that includes a middle frame section that frames and supports an artificial central leaflet. The artificial central leaflet is configured to cover a middle region of the first native leaflet. The middle frame section includes a bend formed between a first region of the artificial central leaflet and a second region of the artificial central leaflet that forms a coaptation plane for coaptation with the second native leaflet. The frame further including two side frame sections extending at opposite sides of the middle frame section and configured to contact side regions of the first native leaflet.

22 Claims, 8 Drawing Sheets

(58) Field of Classification Search
CPC .... A61F 2/2457; A61F 2/2445; A61F 2/2454;
A61F 2/2409; A61F 2/24; A61F 2/2412;
A61F 2/2442
See application file for complete search history.

(56) References Cited

U.S. PATENT DOCUMENTS

| | | | |
|---|---|---|---|
| 9,592,121 B1* | 3/2017 | Khairkhahan | A61B 17/064 |
| 9,610,163 B2* | 4/2017 | Khairkhahan | A61F 2/246 |
| 9,629,720 B2* | 4/2017 | Nguyen | A61F 2/2427 |
| 10,166,098 B2* | 1/2019 | Khairkhahan | A61B 17/0401 |
| 10,182,908 B2* | 1/2019 | Tubishevitz | A61F 2/2418 |
| 10,478,303 B2* | 11/2019 | Khairkhahan | A61F 2/2466 |
| 10,500,048 B2* | 12/2019 | Khairkhahan | A61B 17/068 |
| 10,531,956 B2* | 1/2020 | Skarsgard | A61F 2/2487 |
| 10,631,871 B2* | 4/2020 | Goldfarb | A61M 25/0147 |
| 10,751,180 B2* | 8/2020 | Schewel | A61F 2/2445 |
| 10,945,842 B2* | 3/2021 | Wei | A61F 2/2466 |
| 10,980,632 B2* | 4/2021 | Burriesci | A61F 2/2427 |
| 11,007,057 B2* | 5/2021 | Pham | A61F 2/243 |
| 11,026,791 B2* | 6/2021 | Genovese | A61F 2/2463 |
| 11,083,572 B2* | 8/2021 | McLean | A61F 2/2412 |
| 11,185,413 B2* | 11/2021 | Basude | A61F 2/2463 |
| 11,285,003 B2* | 3/2022 | Duffy | A61F 2/2454 |
| 11,337,801 B2* | 5/2022 | Iyer | A61F 2/2436 |
| 11,432,928 B2* | 9/2022 | Mohl | A61F 2/246 |
| 11,464,634 B2* | 10/2022 | Khairkhahan | A61B 17/064 |
| 11,510,777 B1* | 11/2022 | Iyer | A61F 2/2427 |
| 11,633,281 B2* | 4/2023 | Kappetein | A61B 5/0215 623/2.36 |
| 11,723,772 B2* | 8/2023 | Dixon | A61F 2/2466 623/1.14 |
| 11,759,321 B2* | 9/2023 | Khairkhahan | A61F 2/2463 623/2.42 |
| 11,883,291 B2* | 1/2024 | Gifford, III | A61F 2/2445 |
| 12,102,532 B2* | 10/2024 | Groothuis | A61F 2/2445 |
| 12,109,116 B2* | 10/2024 | Khairkhahan | A61B 17/064 |
| 12,150,856 B2* | 11/2024 | Khairkhahan | A61F 2/2463 |
| 2006/0058871 A1* | 3/2006 | Zakay | A61F 2/246 623/2.18 |
| 2008/0071365 A1* | 3/2008 | Ley | A61F 2/2442 623/2.11 |
| 2014/0243968 A1* | 8/2014 | Padala | A61F 2/2457 623/2.36 |
| 2015/0119981 A1* | 4/2015 | Khairkhahan | A61F 2/2454 623/2.36 |
| 2015/0366666 A1 | 12/2015 | Khairkhahan | |
| 2016/0317290 A1* | 11/2016 | Chau | A61F 2/246 |
| 2017/0049571 A1* | 2/2017 | Gifford, III | A61F 2/2463 |
| 2017/0189186 A1* | 7/2017 | Mohl | A61F 2/2454 |
| 2017/0252162 A1* | 9/2017 | Kuehn | A61F 2/2448 |
| 2018/0325663 A1* | 11/2018 | Taylor | A61F 2/2412 |
| 2019/0029826 A1* | 1/2019 | Zeitani | A61F 2/2445 |
| 2019/0060072 A1 | 2/2019 | Zeng | |
| 2019/0358034 A1* | 11/2019 | Tabata | A61F 2/2415 |
| 2019/0388220 A1* | 12/2019 | Vidlund | A61F 2/2412 |
| 2020/0205978 A1* | 7/2020 | Padala | A61F 2/246 |
| 2020/0237506 A1* | 7/2020 | Christianson | A61F 2/2439 |
| 2021/0275301 A1* | 9/2021 | Kumar | A61F 2/2418 |
| 2021/0330461 A1* | 10/2021 | Bapat | A61F 2/2457 |
| 2021/0338427 A1* | 11/2021 | Zeng | A61F 2/2466 |
| 2021/0361430 A1* | 11/2021 | Herman | A61F 2/2445 |
| 2022/0039944 A1* | 2/2022 | Khairkhahan | A61F 2/2454 |
| 2022/0087816 A1* | 3/2022 | Ratz | A61F 2/2418 |
| 2022/0096234 A1* | 3/2022 | Sorajja | A61F 2/2454 |
| 2022/0096236 A1* | 3/2022 | Guidotti | A61F 2/2463 |
| 2022/0160499 A1* | 5/2022 | Miyashiro | A61F 2/246 |
| 2022/0160508 A1* | 5/2022 | Miyashiro | A61F 2/2454 |
| 2022/0175523 A1* | 6/2022 | Dibie | A61F 2/2418 |
| 2022/0273433 A1* | 9/2022 | Kuck | A61F 2/2454 |
| 2023/0270549 A1* | 8/2023 | Guidotti | A61F 2/2457 623/2.11 |
| 2023/0363912 A1* | 11/2023 | Herman | A61F 2/2457 |
| 2024/0041603 A1* | 2/2024 | Guidotti | A61B 17/0401 |
| 2024/0081990 A1* | 3/2024 | Lally | A61F 2/2436 |
| 2024/0122709 A1* | 4/2024 | Freschauf | A61F 2/246 |
| 2024/0148507 A1* | 5/2024 | Scheinblum | A61B 17/1227 |
| 2024/0156591 A1* | 5/2024 | Pham | A61F 2/2418 |
| 2024/0180704 A1* | 6/2024 | Gifford, III | A61F 2/2445 |
| 2024/0207045 A1* | 6/2024 | Orlov | A61F 2/2436 |
| 2024/0225837 A1* | 7/2024 | Martin | A61F 2/2421 |
| 2024/0315835 A1* | 9/2024 | Oba | A61F 2/2418 |
| 2024/0335287 A1* | 10/2024 | Chau | A61F 2/2466 |
| 2024/0335288 A1* | 10/2024 | Ruban | A61F 2/2457 |
| 2024/0390136 A1* | 11/2024 | Sands | A61F 2/2439 |
| 2024/0423797 A1* | 12/2024 | Oberwise | A61F 2/2436 |
| 2024/0423799 A1* | 12/2024 | Entis | A61F 2/246 |
| 2025/0025300 A1* | 1/2025 | Chang | A61F 2/2454 |
| 2025/0025301 A1* | 1/2025 | Weigler | A61F 2/246 |

OTHER PUBLICATIONS

International Preliminary Report on Patentability received in PCT/IB2022/061323 dated Jul. 5, 2023, p. 24.

* cited by examiner

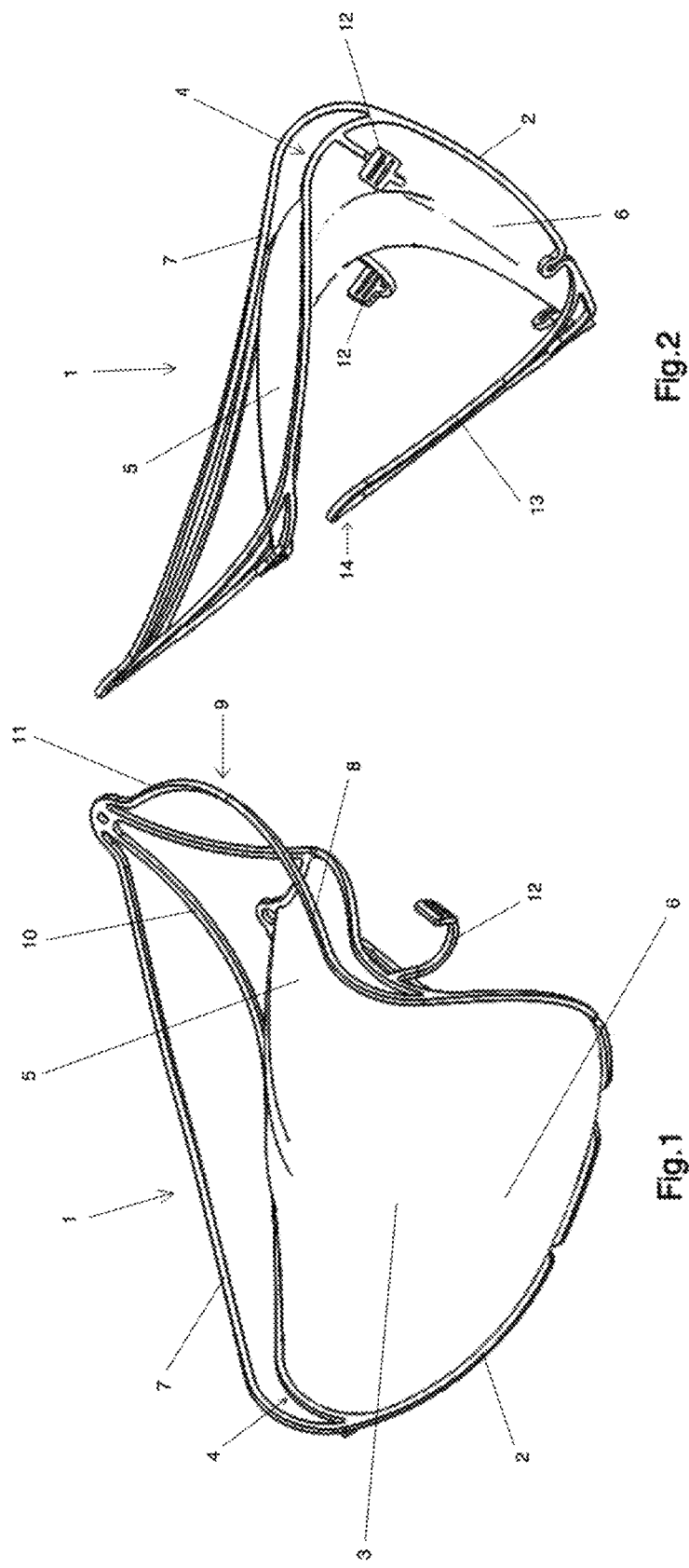

IMPLANT FOR IMPROVING COAPTATION OF AN ATRIOVENTRICULAR VALVE

CROSS-REFERENCE TO RELATED APPLICATIONS

The present application is a national phase application of PCT Application No. PCT/IB2022/061323, filed Nov. 23, 2022, entitled "IMPLANT FOR IMPROVING COAPTATION OF AN ATRIOVENTRICULAR VALVE", which claims the benefit of European Patent Application No. 21020620.7, filed Dec. 7, 2021, each of which is incorporated by reference in its entirety.

BACKGROUND OF THE INVENTION

1. Field of the Invention

The invention relates to an implant for improving coaptation of an atrioventricular valve in a human heart.

2. Description of the Related Art

Atrioventricular valves are membranous folds that prevent backflow from the ventricles of the human heart into the atrium during systole. The valves are anchored within the ventricular cavity by chordae tendineae, which prevent the valves from prolapsing into the atrium when they close. The chordae tendineae are attached to papillary muscles that cause tension to better hold the valve. Together, the papillary muscles and the chordae tendineae constitute the subvalvular apparatus.

The human heart comprises two atrioventricular valves, the mitral valve and the tricuspid valve. The mitral valve allows the blood to flow from the left atrium into the left ventricle. The tricuspid valve is located between the right atrium and the right ventricle.

The mitral valve has an annulus and two leaflets that are each divided into several scallops. The anterior leaflet has three scallops, namely A1, A2 and A3, and the posterior leaflet has three scallops, namely P1, P2 and P3. The anterior and posterior leaflet of the mitral valve are divided by the anterolateral and posteromedial commissure.

The tricuspid valve has three leaflets.

Engagement of the corresponding surfaces of the opposed leaflets against each other, such as, e.g., the engagement of the anterior and posterior leaflet of the mitral valve, is decisive for providing proper valve closure.

Native heart valves become dysfunctional for a variety of pathological causes. Failure of the leaflets to properly close during ventricular systole is known as malcoaptation and causes a backward flow of blood through the valve from the ventricle into the atrium, i.e., in the wrong direction. This physiological process is called regurgitation.

Malcoaptation is often caused by a dilatation of the annulus. Another cause for malcoaptation may be an excessive motion of the leaflet structures, which is due to local elongation or rupture of the chordae tendineae and resulting in a prolapse of parts of the leaflet into the atrium. A restriction in motion of the leaflet structures may also result in malcoaptation.

Heart valve regurgitation may result in cardiac failure, decreased blood flow, lower blood pressure, and/or a diminished flow of oxygen to the tissues of the body.

Mitral regurgitation especially causes an undesired backflow of blood from the left atrium to the pulmonary veins, which in turn may cause congestion and backward heart failure.

One of the main targets in clinical therapy of dysfunctional heart valves is hence to restore proper valve closure.

Proper valve closure may be achieved by complete or partial replacement of the dysfunctional, native heart valve with an artificial heart valve prosthesis.

There are two main types of artificial heart valves, namely mechanical-type and tissue-type valves.

The mechanical-type heart valves make use of mechanical pivoting closure means, which are supported by a base structure and therewith enable coaptation and unidirectional blood flow.

The tissue-type valves have flexible leaflets supported by abase structure and projecting into the flow stream. Tissue-type valves show similar function as native human heart valves and mimic their natural flexing action to coapt against each other.

The instant invention aims at improving state of the art heart implants such that valve closure and valve opening are effectively restored by artificial means, which perfectly mimic native anatomical structures and thereby effectively prevent prolapse of the native leaflet into the atrium.

Further, the present invention aims at providing an improved implant, which effectively withstands the operating forces prevailing in the heart and which is easily to deploy at its target site.

The implant according to the invention also aims at improving state of the art implants such that normal leaflet motion is reproduced, i.e., such that the implant does not restrict leaflet motion of the native leaflet opposed to the implant, and such that the implant does not encourage excessive motion of the opposed leaflet.

Furthermore, the implant according to the invention shall attend to a major problem in failed surgical heart valve repair and interventional valve replacement, i.e., not to restrict blood flow and obstruct the left ventricular outflow tract.

Further, the implant shall correct a variety of mitral pathologies, i.e., primary and secondary mitral regurgitation, and mitral prolapse or restrictive mitral function.

In addition, the implant according to the invention is designed to be easy to use, safe, and efficient, enabling a shorter, low-risk surgical intervention and significantly improving patients' recovery, thereby reducing the duration of hospitalization.

SUMMARY OF THE INVENTION

In order to solve the above objectives, the invention provides an implant for improving coaptation of an atrioventricular valve in a human heart, the atrioventricular valve having a first and a second native leaflet, an anterolateral and posteromedial commissure between the first and the second native leaflet, and an annulus adjacent a wall of an atrium of the heart, whereby the implant comprises a frame that comprises a middle frame section that frames and supports an artificial central leaflet, the artificial central leaflet being arranged and configured to cover a middle region of the first native leaflet, wherein the middle frame section comprises a bent region, in which a bend is formed between a first region of the artificial central leaflet and a second region of the artificial central leaflet that forms a coaptation plane for coaptation with the second native leaflet, the frame further comprising two side frame sections extending at opposite sides of the middle frame section and arranged and configured to contact side regions of the first native leaflet.

The side regions of the first native leaflet in the sense of the invention are to be understood to be, e.g., the anterolateral and posteromedial commissure of the mitral valve or the lateral edges of scallops P1 and P3 of the mitral valve.

The invention is based on the idea that dysfunctional valve closure and opening are best restored with an implant, which mimics native leaflet function in an utmost realistic way. This effect may only be achieved by an implant, which provides a sufficient coaptation surface during systole and which allows for sufficient blood flow during diastole.

To enable an anatomically correct reproduction of a native leaflet, the implant according to the invention is designed such that it covers the dysfunctional native leaflet to a large degree and extends into the commissures, and such that it comprises a bent region, namely a bulge, which is, after having been implanted, oriented towards the opposite native leaflet with which coaptation is to be restored. Thereby the implant according to the invention perfectly mimics the natural curvature of the diseased native leaflet, e.g., the native shape of scallops P1, P2 and P3 of the mitral posterior leaflet.

For achieving coverage of the dysfunctional native leaflet, the middle frame section comprising the artificial central leaflet structure fully covers the middle region of the dysfunctional native leaflet (e.g., scallop P2 and parts of scallops P1 and P3 of the posterior leaflet of the mitral valve), and the side frame sections, which extend at the opposite sides of the middle frame section extend over the side regions of the native valve (e.g., extend over scallops P1 and P3 of the posterior leaflet of the mitral valve).

Preferably, the artificial leaflet forms a coaptation plane with the opposing native leaflet from the anterolateral commissure to the posteromedial commissure with a height of at least 6 mm.

The side frame sections of the implant are arranged and configured such that the side regions of the dysfunctional native leaflet are contacted, i.e., the side regions of the implant extend to and preferably into the anterolateral and posteromedial commissure of the native heart valve.

In the region of the commissures, tissue ingrowth of the lateral edges of the side frame sections takes place, which enables permanent fixation of the implant to the native heart tissue. Thereby, the implant according to the invention provides for a stable positioning within the heart without the need for active mechanical fixation, such as anchors, which would penetrate and hence injure the cardiac tissue.

To provide for an improved stability of the implant during systole, the frame preferably comprises a resting frame section that is configured to rest against the wall of the atrium adjacent the valve. By its contact with the atrial wall, the resting frame section prevents prolapse of the implant into the atrium.

The resting frame section is preferably arranged in a plane that encloses an angle of 90-135° with a plane of the first region of the artificial central leaflet. Said configuration helps to withstand pressures of varying intensity, which act on the valve during systole and diastole, due to which the implant tends to swing back and forth. By the arrangement of the resting frame section in an angle of 90-135°, the swinging movement is reduced and the resting frame is held in tight contact with the wall of the atrium during the swinging movement of the implant, thereby attenuating the same.

According to a preferred embodiment, the first region of the artificial central leaflet comprises a resting extension that encloses an angle of 90-135° with a plane of the first region of the artificial central leaflet.

The preferred combination of the resting frame section and the resting extension of the artificial leaflet, which covers the individual structures, which build the frame of the resting frame section, better holds the implant in place than only the resting frame section.

Hence, if compared to the resting frame section, the resting extension of the artificial leaflet enables the resting frame section to be even more stable, because the extension provides a larger surface for resting against the wall of the atrium. Thereby, the load acting on the atrium wall is distributed over a large area, so that the risk of injuries within the heart is reduced, and punctual penetration of the heart tissue is effectively prevented.

To allow for tissue ingrowth, the resting frame section in its distal region/the resting extension is preferably built as a wing-like structure or is connected to/covered with a cushion-like element.

Preferably, the implant may comprise a plurality of resting frame sections and/or resting extensions, e.g., two, three or four.

The resting frame section preferably connects the side frame sections with each other.

Besides the tissue ingrowth, which occurs at the lateral edges of the side frame sections of the implant, which grow into the commissural tissue, the ingrowth of the resting frame section into the atrial tissue provides an additional fixation point, which enables an even higher stability.

Preferably, the resting frame section only grows into the atrial tissue in said area of the implant, where the structures, which form the resting frame section, taper towards each other.

Preferably, the resting frame section is made of a plurality of wires or metal components.

Preferably, a single wire forms the resting frame section and the side frame sections, said single wire extending from one side of the middle frame section to an opposite side of the middle frame section. Thereby, the side frame sections do not only enhance tissue ingrowth into the commissural tissue, but also provide for a supporting function.

The side frame sections preferably meet the middle frame section at the bent region thereof.

According to a preferred embodiment, the middle frame section and the side frame sections are formed integral with one another. Such integral structure provides for an enhanced foldability and deployability of the implant.

To provide an even more improved foldability and deployability of the implant, the whole implant may preferably be built as a one-piece structure, whereby the folding, which is needed for placing the implant into a delivery catheter, and the deployment, which is needed for providing the implant in its desired shape within the heart, is much easier to perform than it is the case with multipart structures, in which the foldability/deployment properties of the implant do not only depend on the frame structure, which is preferably built by a plurality of interconnected wires, but also on the connection points between the individual parts of the frame structure.

Preferably, the side frame sections each at least partially frame and support an artificial side leaflet being arranged and configured to cover a side region of the first native leaflet.

Thereby not only the middle frame section of the implant is covered by an artificial leaflet structure, but also the side frame sections, which provides for the dysfunctional native leaflet to be fully covered by an artificial leaflet structure.

Said preferred embodiment provides a sufficient coaptation surface during systole, which enables restoration of the impaired valve and proper valve closure.

The artificial leaflet structures may preferably be fixed to the frame over their complete circumference.

Alternatively, the artificial leaflet structures may only be fixed to the frame on certain points thereof, e.g., at the proximal end of the frame. Said alternative embodiment results in an artificial leaflet, which moves independently from the frame of the implant, thereby providing the implant with a high degree of normal anatomical function.

For enhancing fixation of the implant to the heart tissue and to provide immediate connection thereto, the implant preferably comprises anchor means that are connected to the frame, preferably to the side frame sections of the frame and preferably configured to penetrate the or engage with the anterolateral and posteromedial commissure from the backside of the first native leaflet, i.e., from the subvalvular, ventricular side.

Thereby the fixation of the implant is not only dependent on the tissue ingrowth of the side frame sections, but is additionally facilitated by anchor means.

The anchor means function as sub-annular support means and are preferably hook- or heart-shaped or have an oval shape, which perfectly fits into the commissures.

Preferably, a plurality of anchor means is provided, such as, e.g., one anchor means on each of the side frame sections, or two, three or more anchor means on each of the side frame sections.

The anchor means are preferably attached to the lateral edges of the side frame sections of the frame, i.e., point perpendicularly outwards from the side frame sections.

Alternatively, the anchor means may be attached to the region of the frame, which together with the central artificial leaflet forms the coaptation plane of the implant. In said case the anchor means do not extend from the lateral edges of the frame, but towards the opposite native leaflet, i.e., extend radially from the side frame sections.

The anchor means may preferably be actuatable to deploy to a deployed configuration and to provide an improved contact with the sub-annular, commissural tissue upon further actuation. The actuation may be achieved by standard means (pushing, pulling, releasing a stay wire etc.).

Preferably, the frame comprises at least one clamping frame section.

The at least one clamping frame section preferably extends from a distal end of the middle frame section and is arranged and configured to extend on a backside of the first native leaflet and to clamp the first native leaflet or the annulus between a clamping end of the at least one clamping frame section and the middle frame section.

Alternatively, the at least one clamping frame extends from a distal end of the restraining means and is arranged and configured to extend on a backside of the first native leaflet and to clamp the first native leaflet or the annulus between a clamping end of the at least one clamping frame section and the restraining means.

In addition to the optional fixation by a plurality of anchor means, which are preferably connected to the side frame sections of the frame and which provide for a first and second anchoring point for the implant to be fixed from the ventricular side, the at least one clamping frame section also provides an anchoring point.

The at least one clamping frame section clamps at least the distal end of the dysfunctional leaflet and hence grabs the free edge of the dysfunctional leaflet.

Alternatively, the at least one clamping frame section may also clamp the dysfunctional leaflet nearly over its entire backside, i.e., the distal end of the at least one clamping frame section is arranged adjacent to the annulus.

A further advantage provided by the at least one clamping frame section is the provided contact of the dysfunctional native leaflet with the ventricular wall. By the at least one clamping frame section, the impaired native leaflet may be pressed towards the ventricular wall and may hence be hindered to interfere with the movement of the other parts of the implant.

Another advantage provided by the at least one clamping frame section is that the implant's artificial leaflet and the restrained native leaflet are connected and form a blood barrier to avoid paravalvular leakage.

According to the above preferred embodiment, the fixation of the implant is not only dependent on tissue ingrowth of the side frame sections or anchoring of the anchor means in the commissural tissue, but is enhanced by a ventricular clamp, i.e., the clamping frame section, which ensures alignment of the implant with the dysfunctional native leaflet and fixes the same to the implant.

By the contact of the clamping frame section with the ventricular wall, the implant further serves to prevent an undesired movement of the implant during the cardiac cycle, such as prolapse of the posterior leaflet into the left atrium.

The implant according to the invention, preferably comprises an atrial part, consisting of the resting frame section, an annular part, consisting of the middle frame section with its artificial central leaflet and the side frame sections, and a ventricular part, consisting of the anchor means and the clamping frame section.

The frame preferably consists of a stent structure, preferably a metal stent structure, a shape-memory alloy, such as, e.g., Nitinol, a wire frame, struts, or is a laser cut material.

Preferably, the frame has a super-elastic shape.

The artificial leaflet structure is preferably made of a polymer, such as polyurethane, polyamide and ePTFE.

The artificial leaflet structure may also comprise a permeable, e.g., porous, or impermeable matrix material.

Preferably, those parts of the artificial leaflet, which are pressed against the heart wall are porous to allow ingrowth into the heart tissue.

To provide for a minimally invasive implantation procedure, the frame together with the artificial central leaflet, and optionally the artificial side leaflets, are deployable from a first position, in which the implant is folded for being arranged within a tubular housing of a delivery device, into a second position, in which the implant is deployed.

The geometric changes of the frame during deployment may aid the engagement of the anchor means with the commissural tissue.

By the small diameter of the implant in its folded state, the implant may be easily deployed to the heart, e.g., using a transvascular approach.

In particular, the implant may also be advanced into the heart by means of a delivery catheter or a deployment instrument transatrially, transseptally, transfemorally or transapically.

Exemplarily, transseptal implantation takes place as follows: A puncture in the femoral vein in the groin is followed by an advancement of a guide sheet into the right heart. The septum between the right and the left atrium is crossed, and a steerable catheter is positioned into the mitral valve. By retracting the catheter, the implant is pushed out from the inside of the catheter and slowly deployed.

The atrioventricular valve may preferably be a mitral valve. The first native leaflet may hence preferably be the posterior leaflet of the mitral valve and the second native leaflet may hence preferably be the anterior leaflet of the mitral valve.

According to a preferred embodiment, the side frame sections frame and support a first and a second artificial side leaflet. Thereby the atrial wall may be covered with the artificial side leaflets in the region adjacent the valve, which provides for further stabilization of the implant.

Preferably, the artificial central leaflet comprises a flexible material, such that the artificial central leaflet is able to expand in size during systole and decrease in size during diastole, whereby the distance between the frame of the implant and the highest point of the bulge of the artificial leaflet structure is increased during systole and decreased during diastole.

Due to their expansion properties, the artificial central leaflet provides a functioning coaptation surface during systole, which enables proper valve closure and hinders backflow of blood from the ventricle into the atrium.

Contrary thereto, the decreasing properties of the artificial central leaflet provide an orifice between the opposing valves, thereby allowing for sufficient blood flow from the atrium to the ventricle during diastole.

The flexible material of the artificial central leaflet enables accommodation of the implant to the native leaflet motion, i.e., the native leaflet is not impaired by the artificial leaflet structure, but supported.

A preferred embodiment provides an artificial leaflet structure, which is made of a compliant membrane, which changes conformations according to the pressure prevailing in the heart, i.e., billows during systole and collapses during diastole.

To mimic the natural shape of, e.g., scallops P1, P2 and P3 of the posterior leaflet of the mitral valve, the artificial central leaflet is preferably built as flexible polymer cup-like coverings.

To enable full coverage of the dysfunctional native leaflet of mitral or tricuspid valves, the artificial central leaflet may preferably comprise a first lateral segment, a middle segment and a second lateral segment. By said preferred embodiment full coverage of the dysfunctional native leaflet by a three-part, i.e., segmented artificial leaflet structure is enabled.

The first lateral segment of the artificial central leaflet may cover scallop P1 of the native, dysfunctional leaflet.

The middle segment of the artificial central leaflet may cover scallop P2 of the native, dysfunctional leaflet.

The second lateral segment of the artificial central leaflet may cover scallop P3 of the native, dysfunctional leaflet.

The three segments are preferably formed as a one-piece leaflet structure or, alternatively may be formed by three individual interconnected leaflet structures.

To better mimic the anatomical structure of scallops P1, P2 and P3 during systole and diastole, the individual segments of the artificial central leaflet are preferably bulgeable structures, whereby the middle segment of the artificial central leaflet may bulge to a larger extent than the lateral segments of the artificial central leaflet.

According to said preferred embodiment, the individual segments of the artificial central leaflet are hence formed as pillow-like structures, which bulge, whereby their bulges increase in size due to the blood pressure during systole resulting in valve closure, and decrease in size due to the blood pressure during diastole resulting in the opening of the valve.

The part of the implant, which overlays the distal end of the dysfunctional leaflet opposite the annulus hence may range in size from small surfaces to large bulges in the membrane, thereby mimicking, e.g., P1, P2 and P3 of the posterior leaflet of the mitral valve.

Alternatively, the distal part of the artificial central leaflet of the implant (e.g., the membrane), may be formed with ripples or curves, which expand during systole, thereby providing a sufficiently large surface area for coaptation. The ripples or curves increase in size during diastole, thereby providing an orifice between the opposing leaflets for enabling adequate blood flow during diastole.

In addition, or alternatively to the compliant membrane of the artificial leaflet, the frame of the implant may be compliant. Compliance of the frame may, e.g., be achieved by thermoforming techniques. For being compliant, the frame may be designed such that one part of the wire frame, e.g., side frame sections, exert a slight outward radial force on the annulus, which ensures maintenance of the contact between the implant and the annulus.

Preferably, the frame is selectively compliant, thereby providing sufficient support for the artificial central leaflet of the implant by being stiff in some of the regions of the frame, whilst still accommodating to changes in valve geometry throughout the cardiac cycle due to flexible regions of the frame.

Selective compliance in the sense of the present invention is to be understood such that the implant shows a higher stability in regions where large support is needed, and is more flexible in regions, which must adapt to the anatomical conditions acting upon the valve. A selectively compliant frame is hence not overpowering native anatomy and the implant is not overpowered by the pressure prevailing in the heart.

The middle segment of the artificial central leaflet structure preferably differs in size from the lateral segments of the artificial central leaflet, which provides for an optimized 3D-shape of the implant, and therefore perfectly mimics the anatomical structure, e.g., mimics scallops P1, P2 and P3 of an unimpaired native mitral valve leaflet, in which scallop P2 is larger in size than P1 and P3.

Alternatively, when the implant is to be used to repair anterior leaflet prolapse, the artificial central leaflet comprises a single component divided in A1, A2 and A3 mimicking structures.

Preferably, the frame comprises a restraining means that extends from the middle frame section into a space arranged between the artificial central leaflet and the first native leaflet so as to lie on the upper side of the first native leaflet.

The restraining means is preferably arranged between the middle frame section and the clamping frame section and hence extends over the upper surface of the dysfunctional leaflet and restrains the same, when the implant is clamped by the clamping frame section from below.

Thereby the impaired leaflet is appropriately fixed to the heart tissue.

The preferred combination of the restraining means and the clamping frame section results in further stabilization of the implant and prevention of the dysfunctional leaflet to prolapse into the atrium.

Further, said combination decreases the risk that the artificial leaflets, e.g., the polymer matrix grows into the heart tissue.

The risk that the native leaflet and the frame section comprising the artificial leaflets grow together, is also decreased.

The restraining means may be formed as an individual part of the frame and extend from the proximal end of the middle frame section towards the distal end of the middle frame section.

Alternatively, the restraining means may be formed as an integral part of the clamping frame section and extend from the proximal end of the middle frame section towards the distally arranged clamping frame section and ends in the clamping frame section.

Preferably, the restraining means comprise at least one oblique segment to squeeze the native leaflet and displace it onto the ventricular wall.

The restraining means preferably extends in parallel to the middle frame section from a hinge section being arranged between the resting frame section and the middle frame section.

The hinge section may be made from an elastic material such that a high degree of flexibility in the region where the hinging occurs is provided. Flexibility in said hinging region is to be understood as the ability of middle frame section to move towards and away from the closing plane of the valve.

Due to the hinge section, the middle frame section, being covered by the artificial central leaflet, is able to move independently from the restraining means.

To prevent leakage of blood from the ventricle in the annular heart region, the restraining means is preferably partly or fully covered with a membrane or mesh.

Said preferred embodiment enables the dysfunctional, native leaflet to be restrained between the clamping frame section and the membrane or mesh covering the restraining means.

Further, the restraining means, preferably covered with the membrane or mesh, serves to press the dysfunctional leaflet towards the ventricular wall, whereby the dysfunctional leaflet is pushed backward against the ventricular wall.

This results in closure of the dead space between the dysfunctional leaflet and the implant, whereby an impermeable joint between the dysfunctional leaflet and the implant is achieved and leakage of blood in the annular region of the native heart valve is prevented, which hinders undesired paravalvular blood flow between the atrium and the ventricle.

Further, said preferred embodiment serves to prevent thrombosis, which may result from blood clotting in the dead space between the dysfunctional leaflet and the implant.

To prevent blood leakage from the ventricle into the atrium, the membrane or mesh covering the restraining means is preferably connected to the distal region of the artificial central leaflet, such that a fluid-tight connection between the restraining means and the artificial central leaflet is formed.

By interconnecting the artificial central leaflet and the membrane-covered restraining means, the space between the artificial central leaflet and the restraining means is sealed impermeably towards the atrium, such that no blood can escape towards the atrium when the valve is closed during systole.

The implant according to the invention may be delivered as follows:

A coaxial tube catheter is equipped with elements to mount the implant according to the invention and to deliver the same transeptally.

By an outer and inner steerable component, the catheter is navigated with the mounted implant to the valve region, in which the implant is to be fixed.

In a first step of delivery, the outer guide catheter enters the left atrium by penetrating the septum, which provides access to the mitral valve.

The inner steerable catheter flexes towards the valve orifice and moves into the ventricle.

As soon as the inner steerable catheter enters the ventricle, the clamping frame section of the implant is exposed from the distal tip of the inner steerable catheter via actuation of the implant delivery system.

The clamping frame section is positioned into the sinus below the leaflet at least in the region of scallop P2 and deployed. In case of at least two clamping frame sections, one clamping frame section may be positioned in the region of scallop P2 and at least one other clamping frame section may be positioned in the region of the scallop P1 and/or P3.

The clamping frame section thereby contacts the subvalvular region of P2, and allows appropriate seating and stable positioning and an ingrowth of the implant from the ventricular side.

As soon as the clamping frame section is engaged with the heart tissue, the further parts of the implant are unsheathed. The middle frame section deploys to overlay the central scallop of the native leaflet and the side frame sections expand towards the commissural regions resulting in anchorage within the commissures. Preferably, the aforementioned frame sections deploy together with the restraining means.

Preferably, a controlled deployment of the implant is enabled by an elongation mechanism:

The implant according to the invention does not deploy by itself, but is held in an elongated, folded form within and/or outside the catheter. When being subsequently released, an active deployment of the individual parts and change in geometry of the implant takes place, i.e., a change from an elongated to an anatomically adapted, e.g., roundish form.

Summarized, the deployment of the implant according to the invention may be executed as follows:

First, the clamping frame section of the implant is deployed in the ventricle.

Second, the other parts of the implant are released to cover the atrial surface of the native leaflet.

Third, the side frame sections comprising the anchor means move towards the commissures of the valve and the anchor means engage with the anterolateral and posteromedial commissure from the ventricular side.

BRIEF DESCRIPTION OF THE DRAWINGS

The invention will now be described in more detail with reference to the attached drawings.

In the drawings,

FIG. 1 and FIG. 2 show a first embodiment of the implant according to the invention.

DETAILED DESCRIPTION

Figure 3:
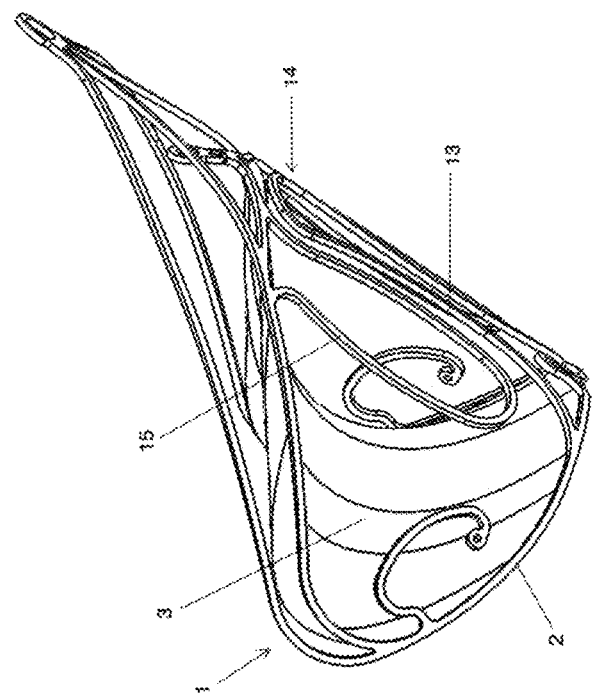
FIG. 3 and FIG. 4 show a second embodiment of the implant according to the invention.

FIG. 1 is an isometric view of a first embodiment of the implant according to the invention, FIG. 2 is a side view of the first embodiment of the implant as depicted in FIG. 1.

In FIG. 1 and FIG. 2 the implant is denoted with arrow 1.

Implant 1 comprises a frame that comprises a middle frame section 2 that frames and supports an artificial central leaflet 3. The artificial central leaflet 3 may cover scallops P1, P2 and P3 of the dysfunctional native valve when being implanted in the heart.

The middle frame section 2 comprises a bent region (denoted by arrow 4), in which a bend is formed between a first region 5 at the proximal end of the implant 1 of the artificial central leaflet 3, which is arranged, i.e., at the end of the implant 1, which is arranged at/adjacent the annulus of the native heart valve when being implanted, and a second region 6 of the artificial central leaflet 3, which is arranged at the distal end of the implant 1, i.e., at the end of the implant, which covers the upper surface of the dysfunctional native leaflet and extends distally from the first region 5 of the implant 1 when being implanted in the heart.

The first region 5 and the second region 6 of the artificial central leaflet 3 form a coaptation plane for coaptating with the second native leaflet, which is opposite to the artificial central leaflet 3 when the implant 1 is implanted in the heart.

The frame further comprises two side frame sections 7 and 8, and a resting frame section (denoted by arrow 9), which connects the side frame sections 7 and 8 with each other.

The side frame sections 7 and 8 extend from either side of the middle frame section 2, thereby forming a superior structure, which is arranged above the lateral edges of the middle frame section 2.

The resting frame section 9 comprises an inner part 10 and an outer part 11, which are integrally formed with each other and provide a larger surface for contacting the atrial wall.

In the preferred embodiment depicted in FIG. 1 and FIG. 2, the frame of the implant 1 is formed by a single structure, e.g., a wire, i.e., the inner part 10 and the outer part 11 of the resting frame section 9, the side frame sections 7 and 8 as well as the middle frame section 2 are formed as a single piece.

As can be taken from FIG. 1 and FIG. 2, the implant 1 further comprises hook-shaped anchor means 12 that are connected to the lateral edges of the middle frame section 2 and extend perpendicularly therefrom.

The anchor means 12 are configured to engage with the anterolateral and posteromedial commissure of the dysfunctional leaflet from the ventricular side.

The frame further comprises a clamping frame section 13, which is connected to the distal end of the middle frame section 2 and extends on the backside of the dysfunctional native leaflet when being implanted in the heart.

The clamping end (denoted by arrow 14) of the clamping frame section 13 clamps the dysfunctional native leaflet adjacent its annular region from the ventricular side, thereby clamping the dysfunctional leaflet between the clamping frame section 13 and the middle frame section 2, whereby the clamping frame section 13 nearly covers the entire inferior surface of the dysfunctional leaflet.

Figure 4:
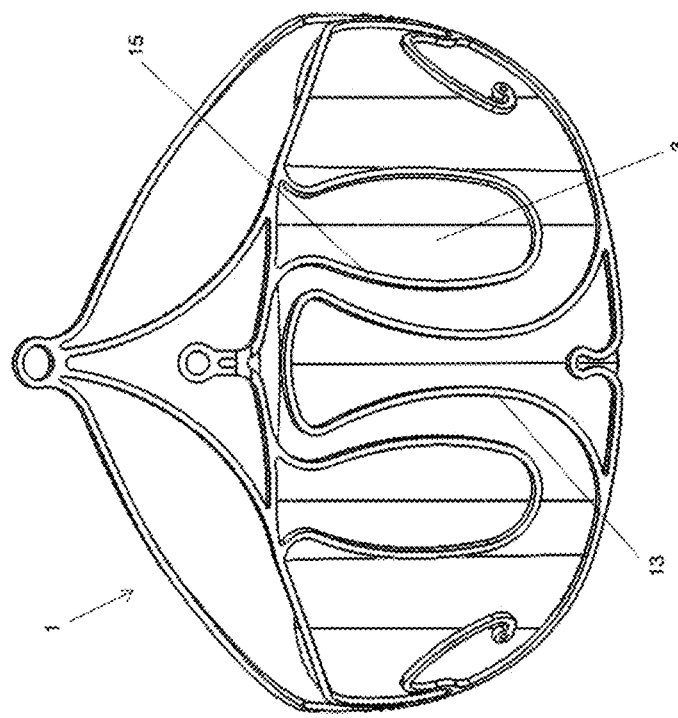

FIG. 3 is a bottom view of a second embodiment of the implant according to the invention, FIG. 4 is an isometric view of the second embodiment of the implant as depicted in FIG. 3.

As can be taken from FIG. 3 and FIG. 4, in order to achieve stabilization of the dysfunctional native leaflet, the frame of the implant 1 comprises a restraining means 15 that extends from the middle frame section 2 into a space between the artificial central leaflet 3 and the clamping frame section 13, and extends on the upper, atrial side of the dysfunctional native leaflet when being clamped by the clamping frame section 13, which extends on the lower, ventricular side of the dysfunctional native leaflet.

According to the second embodiment depicted in FIG. 3 and FIG. 4, the restraining means 15 is designed as a two-loop, integral structure, which forms an individual part of the frame and extends from the proximal end of the middle frame section 2 towards the distal end of the middle frame section 2.

Figure 5:
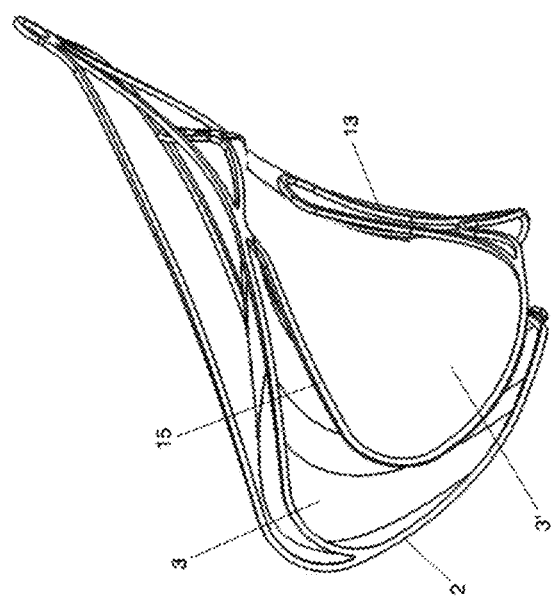
FIG. 5 and FIG. 6 show a third embodiment of the implant according to the invention.
Figure 6:
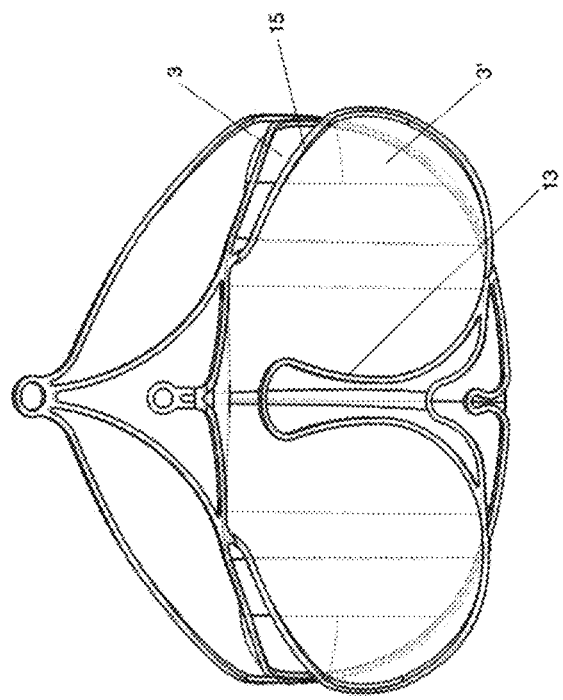

FIG. 5 is a bottom view of a third embodiment of the implant according to the invention, FIG. 6 is an isometric view of the third embodiment of the implant as depicted in FIG. 5.

In case of the third embodiment depicted in FIG. 5 and FIG. 6, the restraining means 15 is formed as an integral part of the clamping frame section 13 and extends from the proximal end of the middle frame section 2 towards the distally arranged clamping frame section 13.

Further, the embodiment depicted in FIG. 5 and FIG. 6 comprises an interconnected artificial leaflet structure, i.e., the artificial central leaflet 3 and the artificial leaflet structure 3', which covers the restraining means 15, are formed as one piece, which prevents the leakage of blood from the ventricle into the atrium and presses the dysfunctional native leaflet against the ventricular wall when being implanted.

Figure 7:
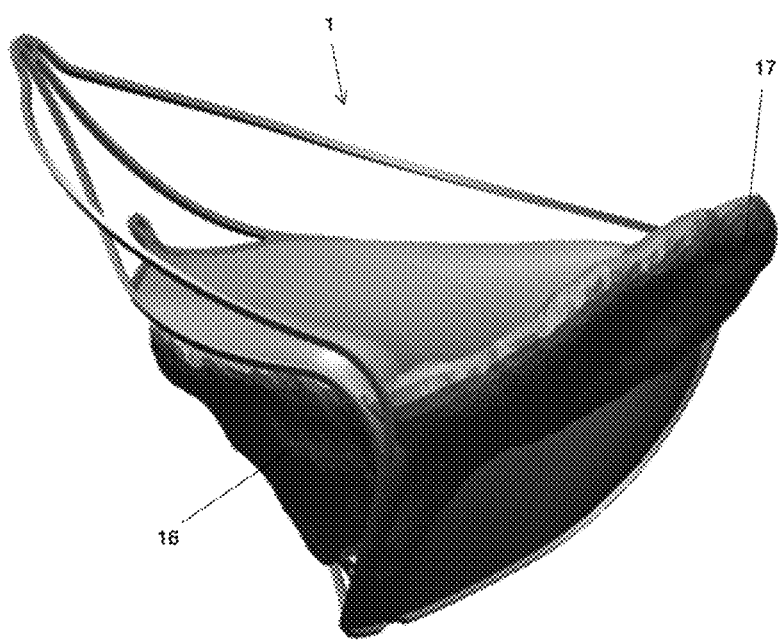
FIG. 7 shows the implant according the invention when being attached to the dysfunctional leaflet and engaging with the native opposing valve.

FIG. 7 shows an isometric view of the implant 1 according to the first embodiment depicted in FIG. 1 and FIG. 2 when being attached to the posterior, dysfunctional leaflet 16 of the mitral valve.

In FIG. 7 the implant 1 attached to posterior valve 16 is in engagement with the opposing anterior leaflet 17 of the mitral valve, whereby proper valve closure during ventricular systole is ensured.

Figure 9:
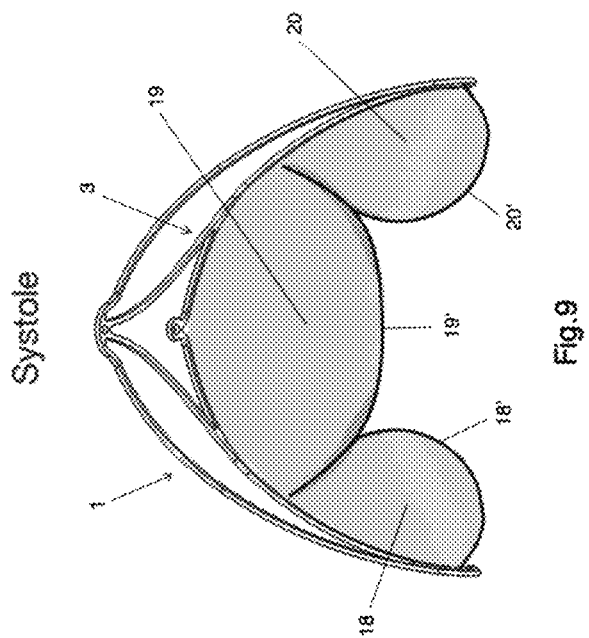
FIG. 8 and FIG. 9 show a fourth embodiment of the implant according to the invention during diastole and systole.
Figure 8:
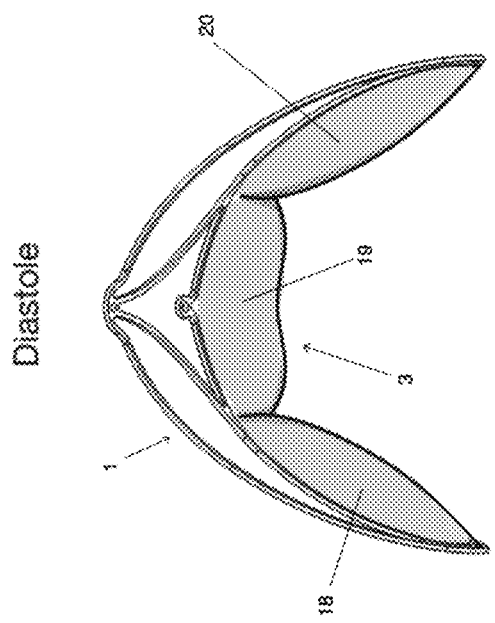

FIG. 8 and FIG. 9 show top views of a fourth embodiment of the implant according to the invention during diastole (left hand side) and systole (right hand side).

According to said preferred embodiment, the artificial central leaflet 3 of the implant 1 is made of a compliant membrane, which comprises three individual segments, namely a first lateral segment 18, a middle segment 19 and a second lateral segment 20. The individual segments change their conformation with the pressure prevailing in the heart, i.e., billow during systole (FIG. 9) and collapse during diastole (FIG. 8).

The expansion during systole provides convex surface areas 18', 19' and 20' during systole for coaptation with the opposed native leaflet.

Figure 11:
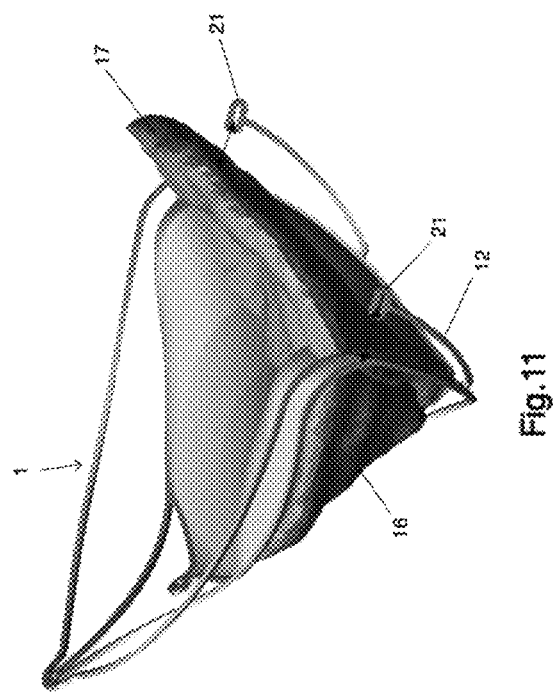
FIG. 10 and FIG. 11 show implants with alternative embodiments of the anchor means.
Figure 10:
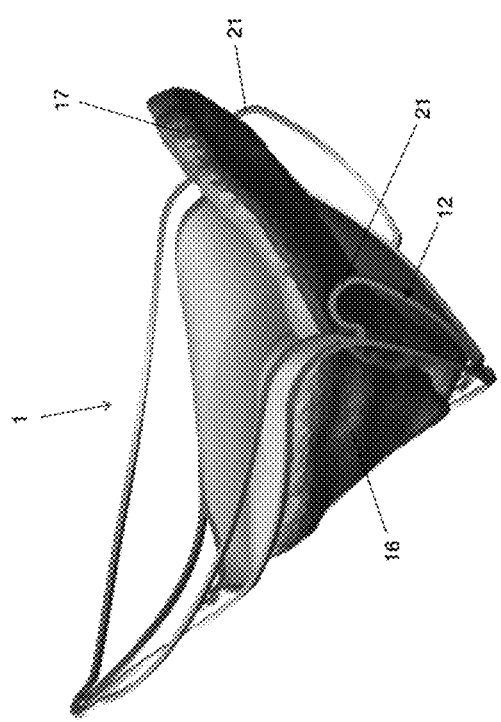

FIG. 10 and FIG. 11 show isometric views of the implant 1 according to the first embodiment depicted in FIG. 1 and FIG. 2 with alternative embodiments of the anchor means 12.

In FIG. 10 and FIG. 11 the anchor means 12 extend radially from the frame of the implant 1 towards the anterior leaflet 17 of the mitral valve when being implanted.

In FIG. 10 the anchor means 12 have an oval shape, in FIG. 11 the anchor means 12 are hook-shaped. The upper ends 21 of the anchor means 12 engage from the ventricular side with the anterolateral and posteromedial commissures of the mitral valve. The anchor means 12 thereby restrain the implant against the hemodynamic forces, which act on the inferior surfaces of the native leaflet.

Figure 12:
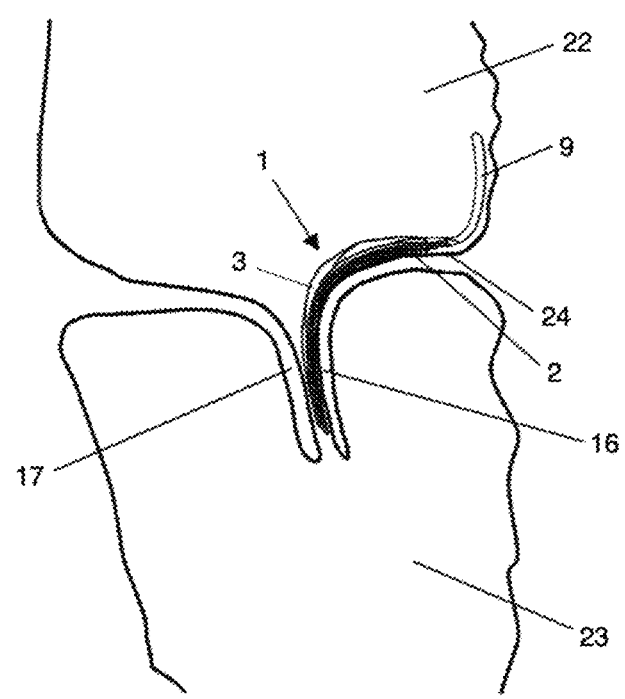
FIG. 12 shows an embodiment of the implant according to the invention when being fixed to the posterior leaflet of the mitral valve during systole.

FIG. 12 shows a cross sectional view of an exemplary embodiment of the implant (denoted by arrow 1) when being fixed to the posterior leaflet 16 of the mitral valve during ventricular systole.

The implant 1 comprises a resting frame section 9 and a middle frame section 2, which comprises an artificial central leaflet 3. The resting frame section 9 presses against the atrial wall and extends towards the annulus 24.

The middle frame section 2 comprising the artificial central leaflet 3 covers the posterior leaflet 16 and extends from the annulus 24 towards the distal end of the posterior leaflet 16.

In ventricular systole, which is depicted in FIG. 12, the mitral valve is closed, i.e., the posterior leaflet 16 being covered by the implant 1 and the opposed anterior leaflet 17 are in engagement with each other, thereby closing the orifice between the left atrium 22 and the left ventricle 23.

Figure 13:
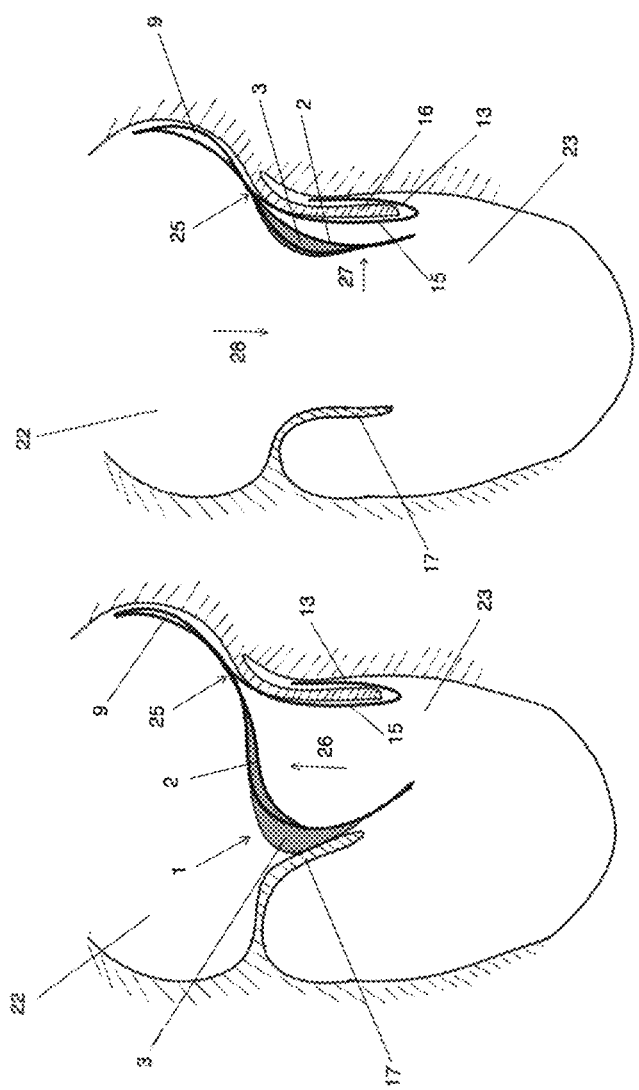
FIG. 13 shows another embodiment of the implant according to the invention when being fixed to the mitral valve during systole and diastole.

FIG. 13 shows another exemplary embodiment of the implant 1 according to the invention when being fixed to the mitral valve during ventricular systole (left hand side) and during ventricular diastole (right hand side).

The implant 1 depicted in FIG. 13 comprises a resting frame section 9, a middle frame section 2 being covered by an artificial central leaflet 3, a restraining means 15, and a clamping frame section 13.

The middle frame section 2 comprising the artificial central leaflet 3 and the restraining means 15 are connected to the resting frame section 9 at a hinge section 25, whereby the restraining means 15 is arranged between the middle frame section 2 and the posterior leaflet 16 and extends from the hinge section 25 in parallel to the middle frame section 2.

The restraining means 15 ends in the clamping frame section 13, which extends towards the annular region of the posterior leaflet 16 thereby covering the inferior surface of the posterior leaflet 16.

The hinge section 25 enables the middle frame section 2 comprising the artificial central leaflet 3 to move independently from the restraining means 15 and the clamping frame section 13, which is attached to the restraining means 15, thereby enabling an independent movement of the artificial central leaflet 3 and a pressing of the dysfunctional, native leaflet 16 against the ventricular wall during systole and diastole.

During systole (cf. left hand side of FIG. 13) the middle frame section 2 with the artificial central leaflet 3 moves towards the anterior leaflet 17 according to arrow 26, whereby the mitral valve closes, i.e., the artificial central leaflet 3 moves towards the closing plane of the valve.

During diastole (cf. right hand side of FIG. 13) the artificial central leaflet 3 moves according to arrow 27 towards the restraining means 15, i.e., the mitral valve opens and blood flow from the atrium 22 to the ventricle 23 according to arrow 28 is enabled. In other words, in diastole the artificial central leaflet 3 moves away from the closing plane of the valve.

The posterior leaflet 16 being clamped between the restraining means 15 and the clamping frame section 13 is pressed against the ventricular wall during systole and diastole, which provides fixation of the dysfunctional posterior leaflet 16 during the cardiac cycle and hence prevents interference with the artificial leaflet structure.

The invention claimed is:

1. An implant for improving coaptation of an atrioventricular valve in a human heart, the atrioventricular valve having a first and a second native leaflet, an anterolateral and posteromedial commissure between the first and the second native leaflet, and an annulus adjacent a wall of an atrium of the heart, the implant comprising:
   a frame that comprises a middle frame section that frames and supports an artificial central leaflet, the artificial central leaflet being arranged and configured to cover a middle region of the first native leaflet; and
   anchor means configured to one of engage with and penetrate the anterolateral and posteromedial commissure;
   wherein the middle frame section comprises a bent region, in which a bend is formed between a first region of the artificial central leaflet and a second region of the artificial central leaflet that forms a coaptation plane for coaptation with the second native leaflet, the frame further comprising two side frame sections extending at opposite sides of the middle frame section and arranged and configured to contact side regions of the first native leaflet; and
   wherein the frame further comprises at least one clamping frame section, which extends from a distal end of the middle frame section and is arranged and configured to extend on a backside of the first native leaflet and to clamp one of the first native leaflet and the annulus between a clamping end of the at least one clamping frame section and the middle frame section.

2. The implant according to claim 1, wherein the frame further comprises a resting frame section that is configured to rest against the wall of the atrium adjacent the valve.

3. The implant according to claim 2, wherein the resting frame section is arranged in a plane that encloses an angle of 90-135° with a plane of the first region of the artificial central leaflet.

4. The implant according to claim 2, wherein the resting frame section connects the side frame sections with each other.

5. The implant according to claim 1, wherein the side frame sections meet the middle frame section at the bent region thereof.

6. The implant according to claim 1, wherein the middle frame section and the side frame sections are formed integral with one another.

7. The implant according to claim 1, wherein the side frame sections each at least partially frame and support an artificial side leaflet being arranged and configured to cover a side region of the first native leaflet.

8. The implant according to claim 1, wherein the anchor means are connected to the frame.

9. The implant according to claim 1, wherein the frame further comprises a restraining means that extends from the middle frame section into a space arranged between the artificial central leaflet and the first native leaflet so as to lie on the upper side of the first native leaflet.

10. The implant according to claim 9, wherein the restraining means is formed as an individual part of the frame and extends from the proximal end of the middle frame section towards the distal end of the middle frame section.

11. The implant according to claim 9, wherein the restraining means is partly or fully covered with a membrane or a mesh.

12. The implant according to claim 11, wherein the membrane or mesh covering the restraining means is connected to the distal end of the middle frame section, which frames and supports the artificial central leaflet, such that a fluid-tight connection between the restraining means and the artificial central leaflet is formed.

13. The implant according to claim 1, wherein the frame consists of a stent structure.

14. The implant according to claim 1, wherein the frame together with the artificial central leaflet is deployable from a first position, in which the implant is folded for being arranged within a tubular housing of a delivery device, into a second position, in which the implant is deployed.

15. The implant according to claim 1, wherein the atrioventricular valve is a mitral valve and the first native leaflet is a posterior leaflet of the mitral valve and the second native leaflet is an anterior leaflet of the mitral valve.

16. The implant according to claim 1, wherein the side frame sections frame and support a first and a second artificial side leaflet.

17. The implant according to claim 1, wherein the artificial central leaflet comprises a flexible material, such that the artificial central leaflet is able to expand in size during systole and decrease in size during diastole.

18. The implant according to claim 1, wherein the artificial central leaflet comprises a first lateral segment, a middle segment and a second lateral segment.

19. The implant according to claim 1, wherein the anchor means are hook shaped.

20. The implant according to claim 1, wherein the anchor means are configured to engage with the anterolateral and posteromedial commissure from a ventricular side of the first native leaflet.

21. An implant for improving coaptation of an atrioventricular valve in a human heart, the atrioventricular valve having a first and a second native leaflet, an anterolateral and posteromedial commissure between the first and the second native leaflet, and an annulus adjacent a wall of an atrium of the heart, the implant comprising:
a frame that comprises a middle frame section that frames and supports an artificial central leaflet, the artificial central leaflet being arranged and configured to cover a middle region of the first native leaflet;
wherein the middle frame section comprises a bent region, in which a bend is formed between a first region of the artificial central leaflet and a second region of the artificial central leaflet that forms a coaptation plane for coaptation with the second native leaflet, the frame further comprising two side frame sections extending at opposite sides of the middle frame section and arranged and configured to contact side regions of the first native leaflet;
wherein the frame further comprises at least one clamping frame section, which extends from a distal end of the middle frame section and is arranged and configured to extend on a backside of the first native leaflet and to clamp one of the first native leaflet and the annulus between a clamping end of the at least one clamping frame section and the middle frame section; and
wherein the first region of the artificial central leaflet comprises a resting extension that encloses an angle of 90-135° with a plane of the first region of the artificial central leaflet.

22. An implant for improving coaptation of an atrioventricular valve in a human heart, the atrioventricular valve having a first and a second native leaflet, an anterolateral and posteromedial commissure between the first and the second native leaflet, and an annulus adjacent a wall of an atrium of the heart, the implant comprising:
a frame that comprises a middle frame section that frames and supports an artificial central leaflet, the artificial central leaflet being arranged and configured to cover a middle region of the first native leaflet;
wherein the middle frame section comprises a bent region, in which a bend is formed between a first region of the artificial central leaflet and a second region of the artificial central leaflet that forms a coaptation plane for coaptation with the second native leaflet, the frame further comprising two side frame sections extending at opposite sides of the middle frame section and arranged and configured to contact side regions of the first native leaflet;
wherein the frame further comprises at least one clamping frame section, which extends from a distal end of the middle frame section and is arranged and configured to extend on a backside of the first native leaflet and to clamp one of the first native leaflet and the annulus between a clamping end of the at least one clamping frame section and the middle frame section;
wherein the frame further comprises a resting frame section that is configured to rest against the wall of the atrium adjacent the valve; and
wherein a single wire forms the resting frame section and the side frame sections, the single wire extending from one side of the middle frame section to an opposite side of the middle frame section.

* * * * *